(12) United States Patent
Matsumoto et al.

(10) Patent No.: US 6,310,249 B1
(45) Date of Patent: Oct. 30, 2001

(54) PROCESS FOR PRODUCING 2-AMINOBENZOPHENONE COMPOUND

(75) Inventors: Hiroo Matsumoto; Takashi Horiuchi, both of Chiba (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 09/743,810

(22) PCT Filed: Jul. 22, 1999

(86) PCT No.: PCT/JP99/03922

§ 371 Date: Jan. 22, 2001

§ 102(e) Date: Jan. 22, 2001

(87) PCT Pub. No.: WO00/05195

PCT Pub. Date: Feb. 3, 2000

(30) Foreign Application Priority Data

Jul. 23, 1998 (JP) ................................................. 10-207910

(51) Int. Cl.[7] .................................................. C07C 211/45
(52) U.S. Cl. ........................... 564/305; 564/315; 564/321; 564/328
(58) Field of Search .................................... 564/305, 315, 564/321, 328, 329, 332

(56) References Cited

U.S. PATENT DOCUMENTS 3,213,139 * 10/1965 Chase et al. .

OTHER PUBLICATIONS

David A. Walsh. "The Synthesis of 2–Aminobenzophenone". Synthesis, 1980; p 677–687.*

Theodora W. Greene. Protective Groups in Organic Synthesis; 1982; p 288, 293, and 331–334.*

* cited by examiner

*Primary Examiner*—Johanni Richter
*Assistant Examiner*—Sikarl A. Witherspoon
(74) *Attorney, Agent, or Firm*—Oblon, Spivak, McClelland, Maier & Neustadt, P.C.

(57) ABSTRACT

A 2-aminobenzophenone represented by formula (2) is obtained by heating an arylsulfonamide represented by formula (1) in the presence of aluminum chloride.

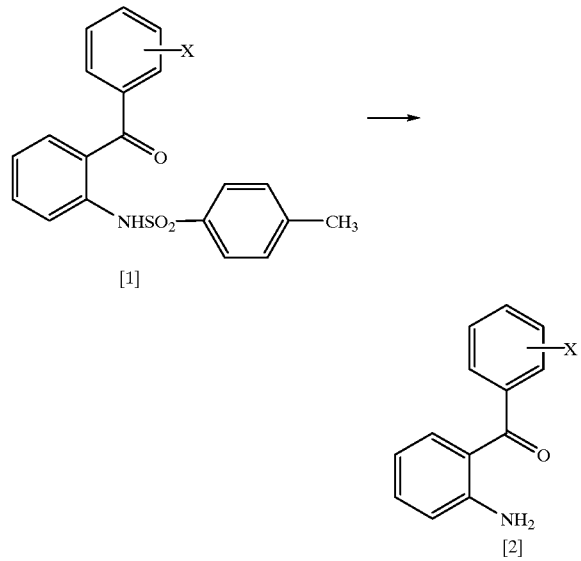

1 Claim, No Drawings

PROCESS FOR PRODUCING 2-AMINOBENZOPHENONE COMPOUND

TECHNICAL FIELD

The present invention relates to a process for producing 2-aminobenzophenones which can be useful intermediates of cholesterol reducing agents (HMG-CoA reductase inhibitors), mental disorders agents and anti-inflammatory agents.

BACKGROUND ART

The quinoline compound represented by formula (3) is disclosed in JP-A-1-279866, EP-A-304063 and U.S. Pat. No. 5,011,930 as a useful cholesterol reducing agent (HMG-CoA reductase inhibitor), and the 2-aminobenzophenone represented by formula (2) (wherein X=4-F) is reported to be useful as its intermediate in Tetrahedron Letters, 1993, vol. 34, p.8267.

[3]

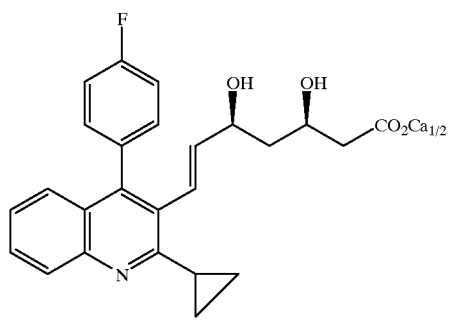

[2]

Likewise, the mental disorder agent represented by formula (4) and the anti-inflammatory agent represented by formula (5) are also synthesized via 2-aminobenzophenones. Therefore, establishment of an industrially advantageous process for their production is of great significance.

[4]

[5]

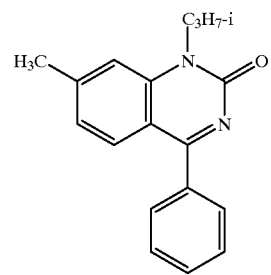

Some processes have been reported for production of 2-aminobenzophenones [review: Synthesis, 677 (1980)]. The process using anthranilic acid as the starting material which comprises formation of an acid chloride after protection of the amino group by a tosyl group and the Friedel-Crafts reaction followed by deprotection has been known long (Org. Synth. Coll. Vol. IV, 34 (1963), Scheme 1) and appreciated for the low raw material cost and the reliability. However, because of the use of concentrated sulfuric acid as the solvent essential for the last detosylation step, the process admittedly has a serious problem with waste liquor disposal from the industrial aspect. Conversely, this means that the production route is pretty fine only if this problem is solved.

Scheme 1

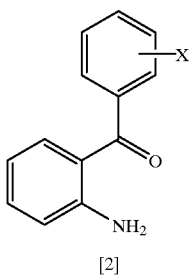

wherein X is a hydrogen atom, a $C_{1-4}$ alkyl group or a halogen atom.

DISCLOSURE OF THE INVENTION

As a result of their extensive research to solve the above-mentioned problem, the present inventors found that heating in the presence of an excess of aluminum chloride subsequent to the Friedel-Crafts reaction facilitates detosylation as shown in Scheme 2 and have accomplished the present invention on the basis of the discovery. The process of the present invention also improves the total yield, for example to 64%, based on anthranilic acid having a tosyl-protected amino group, in the case of the compound (2) (X=4-F) which is an intermediate of the cholesterol reducing agent (HMG-CoA reductase inhibitor)represented by formula (3). A cutback in materials and a great improvement in production efficiency can be accomplished by conducting the three steps starting from the formation of the acid chloride in the same solvent continuously.

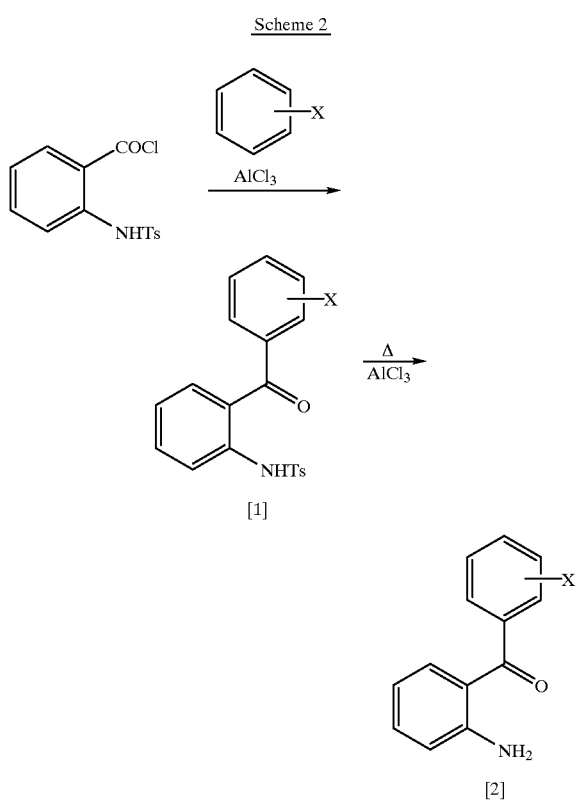

Namely, the present invention relates to a process for producing a 2-aminobenzophenone represented by formula (2) characterized by heating an arylsulfonamide represented by formula (1) in the presence of aluminum chloride.

The process of the present invention dispenses with the conventional need for concentrated sulfuric acid in detosylation and is advantageous in respect of waste liquor disposal. The process of the present invention also makes it possible to conduct the Friedel-Crafts reaction and detosylation without a break and contributes to a cutback in material and a great improvement in production efficiency in production of a medical intermediate represented by formula (2).

BEST MODE FOR CARRYING OUT THE INVENTION

Now, the process of the present invention will be described.

As the reaction solvent used in the formation of the chloride of tosylanthranilic acid, although a halogenated aliphatic hydrocarbon such as dischloroethane could be used as disclosed in Org. Synth. Coll. Vol. IV mentioned above, it is advantageous in terms of efficiency to use a high-boiling substituted aromatic hydrocarbon (having a halogen atom or a nitro group as the substituent) such as ortho-dichlorobenzene so that the resulting phosphorus oxychloride can be distilled off at reduced pressure, leaving the solvent behind. The subsequent Friedel-Crafts reaction and detosylation reaction can be conducted directly in the solution of the acid chloride in the substituted aromatic hydrocarbon.

The formation of the acid chloride can be carried out at temperatures of from 0 to 100° C., but it is preferred to add phosphorus pentachloride at from 15 to 30° C. and then complete the reaction at elevated temperatures of from 70 to 90° C. The sequential Friedel-Crafts reaction and detosylation reaction are preferred to be carried out by adding aluminum chloride at from 15 to 30° C., continuing the reactions at from 40 to 60° C. and completing the reaction at elevated temperatures of from 70 to 90° C. Although from 1.1 to 1.2 times as many moles of aluminum chloride is sufficient for the Friedel-Crafts reaction, it is preferred to use from 2 to 4 times as many moles of aluminum chloride in order to proceed to the detosylation without a break. An excess of aluminum chloride, though not being influential in the reactions, would add to the burden of post-treatment. Conversely, shortage of aluminum chloride would be an obstacle to completion of the reactions.

In the meantime, it is advantageous in terms of efficiency to isolate and purify the 2-aminobenzophenone in the form of the methanesulfonate salt in case that contamination with the following by-product occurs.

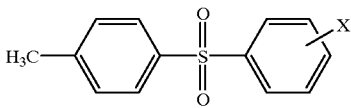

Now, the present invention will be described in further details with reference to Examples. However, the present invention is by no means restricted to these specific Examples.

REFERENCE EXAMPLE 1

Preparation of Tosylanthranilic Acid

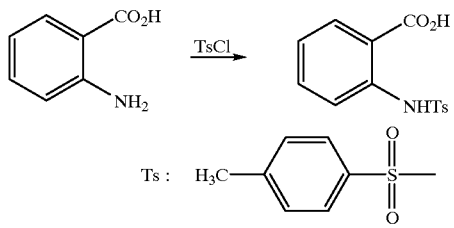

In a 1 L reaction flask equipped with a condenser, 34.25 g (0.25 mol) of anthranilic acid, 411 g of water and 63.59 g (0.6 mol) of sodium carbonate were heated. The resulting reaction solution was maintained at an inner temperature of 78° C. for 30 minutes and then cooled to 67° C., and 57.2 g (0.3 mol) of tosyl chloride was added in two portions. The reaction solution gradually generated heat upon addition of tosyl chloride and turned homogeneous at 78° C. The reaction solution was aged at 80° C. for 1 hour. Crystals started to separate out in the first ten or so minutes of the aging. The completion of the reaction was confirmed by liquid chromatography, and the reaction solution was carefully neutralized with concentrated hydrochloric acid and allowed to cool. The crystals were collected by filtration at room temperature and washed with 100 ml of dilute hydrochloric acid at pH 3 and with 125 ml of water. Recrystallization from 247 g of n-propanol afforded 56.97 g of tosylanthranilic acid in a 78.3% yield.

Example 1

Preparation of 2-amino-4'-fluorobenzophenone

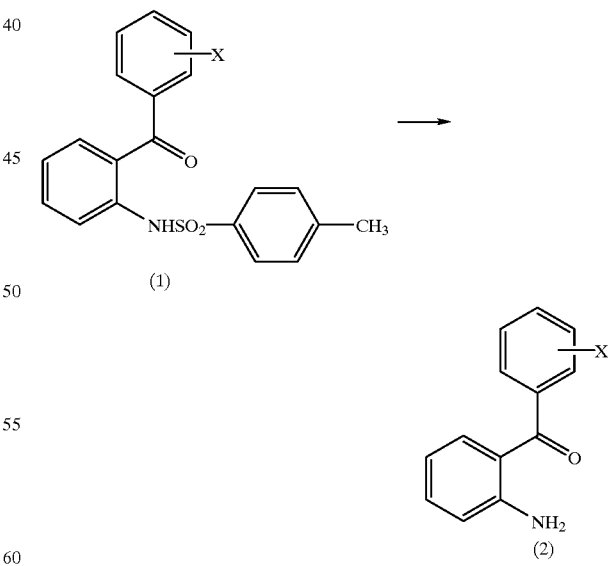

In a 1 L reaction flask equipped with a condenser, 56.97 g (0.196 mol) of tosylanthranilic acid was suspended in 372.0 g of o-dichlorobenzene (hereinafter referred to as DCB), and 42.81 g (0.206 mol) of phosphorus pentaoxychloride was added all at once. The reaction solution was stirred at room temperature for about 1.5 hours, generating noticeable slight heat. Then, the reaction solution was heated and maintained at an inner temperature of 85° C. for 1 hour. The reaction solution turned homogenous upon heating immediately, and generation of hydrogen chloride gas was observed as the reaction proceeded. The reaction solution was aged at an inner temperature of 85° C. for 1 hour and then allowed to cool, and the resulting phosphorus oxychloride and the DCB were distilled off under reduced pressure in a total amount of 90 g. The reminder was allowed to cool to room temperature, and 78.5 g of aluminum chloride and 47 g of fluorobenzene were added. Sight heat generation was recognized, and a homogeneous solution was formed when the aluminum chloride melted at 50° C. The reaction solution was heated to an inner temperature of 80° C. and maintained at the same temperature for 3 hours. The completion of the reaction was confirmed by liquid chromatography, and the reaction solution was allowed to cool and poured into 700 g of ice-cold water carefully so that the liquid temperature would not exceed 30° C. The solution was heated to an inner temperature of from 70 to 80° C. to homogeneity and allowed to separate while it was hot. The aqueous layer was extracted with 150 g of DCB at 70° C. again, and the organic layers was combined and washed with 250 g of water. After 250 g of DCB was distilled off under reduced pressure, the organic layer was allowed to cool. It was recognized that crystals started to separated out at about 40° C. Aging of the crystals at from 0 to 5° C. for 3 hours followed by filtration, washing with 25 g of cold DCB and drying at 60° C. under reduced pressure afforded 26.9 g of the desired product in a 63.8% yield. m.p. 129–130° C.

What is claimed is:

1. A process for producing a 2-aminobenzophenone represented by formula (2) comprising:

heating an arylsulfonamide represented by formula (1) in the presence of aluminum chloride:

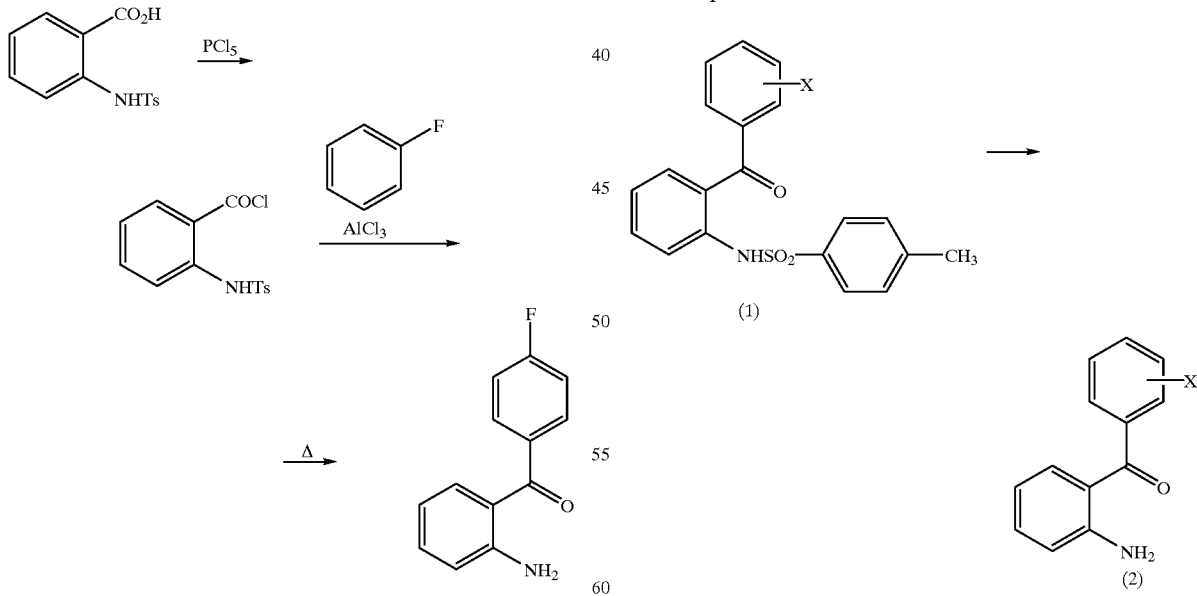

wherein X is a hydrogen atom, a $C_{1-4}$ alkyl group or a halogen atom.

* * * * *